United States Patent [19]

Bode et al.

[11] Patent Number: 4,994,367

[45] Date of Patent: Feb. 19, 1991

[54] EXTENDED SHELF LIFE PLATELET PREPARATIONS AND PROCESS FOR PREPARING THE SAME

[75] Inventors: Arthur P. Bode, Greenville, N.C.; William A. L. Heaton, Norfolk; Stein Holme, Virginia Beach, both of Va.; David T. Miller, Parkland, Fla.

[73] Assignee: East Carolina University, Greenville, N.C.

[21] Appl. No.: 255,621

[22] Filed: Oct. 7, 1988

[51] Int. Cl.$^5$ ............................................. A01N 1/02
[52] U.S. Cl. ......................................... 435/2; 424/532
[58] Field of Search ...................... 435/2; 424/101, 532

[56] References Cited

U.S. PATENT DOCUMENTS

| | | |
|---|---|---|
| 4,447,415 | 5/1984 | Rock et al. .......................... 424/101 |
| 4,568,676 | 2/1986 | Smith ................................. 514/258 |
| 4,595,674 | 6/1986 | Tschesche et al. ..................... 514/9 |
| 4,695,460 | 9/1987 | Holme ................................ 424/101 |
| 4,713,369 | 12/1987 | Stuber ............................... 514/18 |
| 4,740,594 | 4/1988 | Mauzac et al. ....................... 536/51 |
| 4,745,116 | 5/1988 | Krantz et al. ....................... 514/230 |
| 4,745,177 | 5/1988 | Fritz et al. ......................... 530/324 |
| 4,747,737 | 5/1988 | Fujii et al. ......................... 540/575 |
| 4,755,379 | 7/1988 | Jozefonvicz et al. .................. 424/83 |
| 4,757,057 | 7/1988 | Fussi et al. ......................... 514/56 |
| 4,761,477 | 8/1988 | Ikekawa et al. ...................... 546/48 |
| 4,764,463 | 8/1988 | Mason et al. ........................ 424/101 |
| 4,767,742 | 8/1988 | Dodt et al. ......................... 514/12 |
| 4,772,686 | 9/1987 | Szelke et al. ....................... 530/331 |

OTHER PUBLICATIONS

Bode, A. et al., "Effects of Plasmin and Thrombin Inhibitors and Surface to Volume Ratio on the Plastic Storage Lesion", *Transfusion* 27, No. 6, 537 (1987).
Bode, A. and D. Miller, "The Use of Thrombin Inhibitors and Aprotinin in the Preservation of Platelets Stored for Transfusion", *J. Lab. Clin. Med.* 113, No. 6, 753 (1989).
Bode, A. and D. Miller, "Metabolic Status of Platelet Concentrates During Extended Storage: Improvement with Pharmacological Inhibitors and Reduced Surface-to-Volume Ratio", *Vox Sang* 57, 19 (1989).
Bode, A., "Platelet Activation May Explain the Storage Lesion in Platelet Concentrates", *Blood Cells* 16, 109 (1990).
Bode, A. P. and Miller, D., *Transfusion*, 25, 461 (1985).
Bode, A. P. et al., "Effects of Plasmin and Thrombin Inhibitors and Surface to Volume on the Platelet Storage Lesion", *Abstract Submittal Form*.
Murphy, S. et al., *Transfusion*, 26, No. 6 (1986).
Mason, J. et al., *Transfusion*, 26, No. 6 (1986).
Holme, S. et al., *British Journal of Haematology*, 66, 233-238 (1987).
Bode, A. P. and Miller, D. T., *J. Lab. Clin. Med.*, 24, 111-118 (1988).
Adams, G. A. and Rock, G., *Transfusion*, 28, 217-220 (1988).
Adams, G. A. et al., *Vox Sang.* 52, 305-312 (1987).
Adams, G. A. et al., *Blood*, 67, 672-675 (1986).
Menitove, J. E., et al., *Transfusion*, 28, 56-58 (1988).

*Primary Examiner*—Sam Rosen
*Attorney, Agent, or Firm*—Bell, Seltzer, Park & Gibson

[57] ABSTRACT

A first aspect of the present invention is a blood platelet preparation comprising blood platelets, an adenylate cyclase stimulator, a phosphodiesterase inhibitor, a thrombin inhibitor, and a plasmin inhibitor. A second aspect of the present invention is a plasma-free platelet storage medium containing dextrose, sodium citrate, sodium bicarbonate, and a platelet activation inhibitor, with a preferred platelet activation inhibitor comprising an adenylate cyclase stimulator in combination with a phosphodiesterase inhibitor. A third aspect of the present invention is a process for producing a plasma-free platelet preparation comprising producing platelet-rich plasma (PRP) from whole blood, adding a platelet activation inhibitor thereto, centrifuging the PRP to deposit the platelets on the bottom of the centrifuge container, removing the platelet-free plasma supernatant therefrom and adding a plasma-free liquid platelet storage medium thereto. A preferred platelet activation inhibitor for the process comprises an adenylate cyclase stimulator in combination with a phosphodiesterase inhibitor.

A preferred adenylate cyclase stimulator is Prostaglandin El, a preferred phosphodiesterase inhibitor is Theophylline, a preferred plasmin inhibitor is Aprotinin, and a preferred thrombin inhibitor is N-(2-naphthylsulfonylglycyl)-D,L-amidinophenylalaninpiperidide.

11 Claims, No Drawings

EXTENDED SHELF LIFE PLATELET PREPARATIONS AND PROCESS FOR PREPARING THE SAME

BACKGROUND OF THE INVENTION

1. Technical Field

The present invention relates to the preservation of blood platelets. Specifically, the present invention concerns (a) blood platelet activation inhibitors, (b) plasma-free platelet storage media containing blood platelet activation inhibitors, and (c) a process for preparing platelets in plasma-free platelet storage media.

2. State of the Art

The use of platelet concentrates in transfusion medicine has become well established during the past thirty years. However, the rapid loss of platelet function during the storage period has greatly complicated management of an effective inventory of platelet concentrates in blood banks. In many settings, the limited shelf life of platelet concentrates has drastically reduced their usage. In order to make platelet transfusion therapy more manageable for blood banks, there has been considerable interest in devising means for diminishing or delaying the loss of platelet function during the storage period. One approach has been in the context of the development of plasma-free platelet storage media. One such media is disclosed in S. Holme, U.S. Pat. No. 4,695,460 (Issued Sept. 22, 1987); see also S. Holme, W. Heaton and M. Courtright, *British J. Hematol.* 66, 233 (1987). Another such media is disclosed in G. Rock and G. Adams, U.S. Pat. No. 4,447,415 (Issued May 8, 1984); *See Also* G. Adams and G. Rock, *Transfusion* 28, 217 (1988); G. Adams et al., *Vox Sano.* 52, 305 (1987); G. Adams et al., *Blood* 67, 672 (1986). Still another such media is disclosed in S. Murphy et al., *Transfusion* 26, 568 (1986)(Abstract).

Another approach has focused on the biochemistry of platelet activation. Platelet activation is caused by a broad variety of events, and concludes in platelet lysis and death. Hence, it would be desireable to regulate platelet activation when long storage life of platelet concentrates is desired. A. Bode and D. Miller, *Transfusion* 25, 461 (1985)(Abstract) report the use of Prostaglandin E-1 (an adenylate cyclase stimulator), theophylline (a phosphodiesterase inhibitor), and either PPACK or Hirudin (Thrombin inhibitors) in combination in platelet concentrates to obtain platelet concentrate shelf lives of up to fifteen days. *See also* A. Bode and D. Miller, *J. Lab. Clin. Med.* 111, 118 (1988)(Reviewing attempts to extend platelet shelf life with platelet activation inhibitors); J. Menitove et al., *Transfusion* 28, 56 (1988)(Reviewing attempts to extend platelet shelf life with platelet activation inhibitors). The challenge in this line of research has been to develop the unique combination of platelet activators which will most effectively extend platelet shelf life.

The present invention is based on our continued research into means for extending platelet shelf life.

SUMMARY OF THE INVENTION

A first aspect of the present invention is a blood platelet preparation. The preparation comprises blood platelets, an adenylate cyclase stimulator, a phosphodiesterase inhibitor, a thrombin inhibitor, and a plasmin inhibitor. The adenylate cyclase stimulator is included in an amount effective to increase the production of adenosine 3', 5'-cyclic phosphate (cAMP) in the blood platelets. The phosphodiesterase inhibitor is included in an amount effective to reduce the degradation of cAMP in the blood platelets. The thrombin inhibitor is included in an amount effective to reduce the stimulation of the blood platelets by thrombin. The plasmin inhibitor is included in an amount effective to reduce the degradation of cell surface proteins on the blood platelets.

A second aspect of the present invention is a sterile, plasma-free platelet storage medium. The medium comprises a physiologically compatible, aqueous electrolyte solution. One liter of this solution has between about 3.0 and about 7.5 grams of dextrose, between about 3.0 and about 6.0 grams of sodium citrate, between about 2.0 grams and about 4.2 grams of sodium bicarbonate, and an activation-inhibiting amount of a platelet activation inhibitor. The platelet storage medium is isotonic and has a pH in a range of between about 6.8 and about 7.4. The platelet storage medium is capable of preserving platelets for at least about 10 days at a temperature of at least about 22 degrees Centigrade. In a preferred embodiment of this storage medium, the platelet activation inhibitor comprises an adenylate cyclase stimulator and a phosphodiesterase inhibitor. The adenylate cyclase stimulator is included in an amount effective to increase the production of cAMP in the blood platelets, and the phosphodiesterase inhibitor is included in an amount effective to reduce the degradation of cAMP in the blood platelets.

A third aspect of the present invention is a process for producing a plasma-free blood platelet preparation from whole blood. In the process, red blood cells are separated from the whole blood to produce platelet-rich-plasma. A platelet activation inhibitor is then added to the platelet-rich-plasma. The platelet-rich-plasma is then centrifuged in a container to produce a platelet-free plasma supernatant in the container and concentrated platelets deposited on the bottom of the container. The platelet-free plasma supernatant is then removed from the container and a plasma-free liquid platelet storage medium added to the container. Preferably, the platelet activation inhibitor used is comprised of an adenylate cyclase stimulator and a phosphodiesterase inhibitor. The adenylate cyclase stimulator is provided in an amount effective to increase the production of cAMP in the blood platelets, and the phosphodiesterase inhibitor is provided in an amount effective to reduce the degradation of cAMP in the blood platelets.

DETAILED DESCRIPTION OF THE INVENTION

Exemplary plasma-free platelet storage media for use in practicing the present invention are disclosed in U.S. Pat. No. 4,695,460 to Holme and U.S. Pat. No. 4,447,415 to Rock et al. The disclosures of these and all other patent references cited herein are to be incorporated herein by reference. Preferred for practicing the present invention are the Media disclosed in U.S. Pat. No. 4,695,460 to Holme at column 5 line 11 through column 9 line 22. Particularly preferred for practicing the present invention is a media comprised of 750 milliliters of Ringer's solution, 170 milliliters of acid citrate dextrose (ACD), 40 milliliters sodium bicarbonate 8.4 percent solution, 5.4 milliliters dextrose 50 percent solution, 0.7 milliliters potassium chloride 22 percent solution, 0.4 milliliters magnesium sulfate 50 percent solution, filled to the volume of one liter with sterile deionized water. In our hands we found it preferable to control the initial pH of the plasma-free platelet concentrate by adding, sterilely, 2.7 milliliters of the sodium bicarbonate 8.4 percent solution per 60 milliliters volume of plasma-free platelet concentrate. The term "Norfolk Media," as used herein, refers to a media as described above except that 170 milliliters of citrate-phosphate-dextrose (CPD) instead of ACD, and the final addition of sodium bicarbonate 8.4 percent solution to the plasma-free platelet concentrate was 2.4 instead of 2.7 milliliters per 60 milliliters volume of plasma-free platelet concentrate.

The term "platelet activation inhibitor," as used herein, includes adenylate cyclase stimulators, phosphodiesterase inhibitors, and thrombin inhibitors. As will be clear from the context of this document, the term "platelet activation inhibitor" is used to describe a single platelet activation inhibiting compound or a composition comprised of two or more platelet activation inhibiting compounds. Thrombin inhibitors are herein considered platelet activation inhibitors because they act to block a signal which will induce platelet activation.

Exemplary phosphodiesterase inhibitors include xanthine, caffeine, theophylline, theobromine, aminophylline, oxtriphylline, dyphylline, pentoxifylline, isobutylmethylxanthine, dipyridamole, and papaverine. See generally Goodman and Gilman's The Pharmacological Basis of Therapeutics, 589–603 (7th ed. 1985) Preferred are methylxanthines, with theophylline being most preferred. Exemplary adenylate cyclase stimulators are Prostaglandin E1, Prostacyclin, Forskolin, and Adenosine. Additional adenylate cyclase stimulators are disclosed in U.S. Pat. No. 4,761,477. The preferred adenylate cyclase stimulator is Prostaglandin E1. Exemplary plasmin inhibitors are aprotinin, C1-inactivator, alpha 2-antiplasmin, alpha 2-macroglobulin, alpha 1-antitrypsin, epsilonaminocaproic acid, and tranexamic acid. Additional plasmin inhibitors are disclosed in U.S. Pat. No. 4,595,674. Prefered is aprotinin. Exemplary thrombin inhibitors are Hirudin, N-(2-naphthylsulfonl-glycyl)-D,L-amidinophenylalaninpiperidide (THROMSTOP), PPACK, and heparin and its active fragments. Other exemplary thrombin inhibitors are disclosed in U.S. Pat. Nos. 4,772,686; 4,767,742; 4,757,057; 4,755,379; 4,746,737; 4,745,177; 4,745,116; 4,740,594; and 4,713,369. Preferred is Thromstop or Hirudin. Most preferred is Thromstop.

The amount of Prostaglandin E1 employed in the present invention is preferably between about 100 and 500 nanomolar, more preferably between about 200 and 400 nanomolar, and most preferably 300 nanomolar in both the platelet-rich-plasma and the plasma-free platelet preparation. The amount of Theophylline is preferably between about 1.6 and 2.2 millimolar, and most preferably 1.9 millimolar, in both the platelet-rich-plasma and the plasma-free platelet preparation. The amount of THROMSTOP is preferably between about 2 and 10 micromolar, and most preferably 6 micromolar, in both the platelet-rich plasma and the plasma-free platelet preparation. The amount of Aprotinin is preferably between about 50 and 1000 Kallikrein Inhibitor Units (KIU)/milliliter, more preferably between about 150 and 500 KIU/ml, and most preferably 348 KIU/ml in both the platelet rich plasma and the plasma-free platelet preparation.

In the process for producing a plasma-free blood platelet preparation of the present invention, it is particularly advantageous that the platelet activation inhibitor added to the platelet-rich-plasma comprise an adenylate cyclase stimulator in an amount effective to increase the production of cAMP in said blood platelets and a phosphodiesterase inhibitor in an amount effective to reduce the degradation of cAMP in said blood platelets. Preferably, the same platelet activation inhibitor added to the platelet-rich-plasma is included in the plasma-free platelet storage medium added to the platelets deposited on the bottom of the centrifugation container after the platelet-free-plasma is removed therefrom. Additional additives to the platelet activation inhibitor, and quantity ranges for these ingredients, are as given above.

We have found that an important factor in determining the shelf life of plasma-free platelet preparations of the present invention is the surface to volume ratio of the container in which the plasma-free platelet preparation is stored. Hence, a further aspect of the present invention is a container having contained therein a sterile plasma-free platelet preparation, the container having a surface to volume ratio of between about 3 to 5 square centimeters per milliliter, or more preferably about 4 square centimeters per milliliter. It is our belief, though we do not wish to be bound thereby, that containers with a surface to volume ratio greater than specified provide too great a surface area against which platelets can collide and thereby become activated, while containers with a smaller surface to volume ratio than specified provide insufficient surface area for the gas exchange required to maintain the living platelets. The term "container," as used in this context, means those containers capable of preserving the sterility of plasma-free platelet preparations stored therein and permitting sufficient gas exchange to avoid suffocation of the platelets, as conventionally used and understood in the blood collection and processing industry.

Preferably, plasma-free platelet preparations of the present invention are stored at room temperature (20–24 degrees Centigrade) until use, rather than refrigerated or frozen, with the shelf life preferably being at least about 15 days.

The present invention is described in greater detail in the examples which follow. These examples are provided for illustrative purposes only, and are not to be taken as limiting.

EXAMPLE 1

Plasmin Inhibitors in Combination with Platelet Activation Inhibitors

Reagents

Hirudin (grade IV from leeches), theophylline (anhydrous), prostaglandin E-1 (synthetic hemisulfate), and aprotinin (10-20 TIU/mg) were purchased from Sigma Chemical Co. (St. Louis, Mo.). Thromstop (Beta-Nas-Gly-p(Am)Phe-Pip) was purchased from American Diagnostica (New York, N.Y.). Sodium heparin (1000 units/mL, porcine), was obtained from Forest Pharmaceuticals (Inwood, N.Y.). Fragmin (low molecular weight heparin, Kabi 2165, 10,000 u/mL) was a gracious gift from Dr. R. Leonardi (Kabi Vitrum, Alameda, Calif.). DABE (di-amidino benzofuranyl ethane) was synthesized and kindly provided by Dr. D. Hesson (du Pont de Nemours, Wilmington, De.). BABIM (bis (5-amidino-2-benzimidazolyl) methane) and 5-amidinoindole were synthesized and kindly provided by Dr. R. Tidwell (Univ. N. Carolina, Chapel Hill, N.C.). ADP (adenosine 5!-diphosphate) was purchased from Bio/Data Corp (Hatboro, Pa.). All other chemicals and buffers were reagent grade or better.

Anticoagulants

Blood was collected from aspirin-free, healthy, volunteer donors into half-unit collection sets (Fenwal code 4R6004, Baxter Travenol Labs, Deerfield, Il.) in which the CPDA-1 anticoagulant had been replaced or supplemented with the above compounds. PGE-1 was first dissolved in absolute ethanol at 1.0 mg/mL, and DABE was dissolved in 50% ethanol at 8 mg/mL. Hirudin, theophylline, aprotinin, Thromstop, Fragmin, BABIM, and 5-amidinoindole were dissolved directly in CPDA-1 removed from the collection bag and sterilely returned through a 0.2 micrometer filter (Acrodisc; Gelman Sciences, Ann Arbor, Mich.). The complete formulations of anticoagulant were as follows (concentrations given for agents in whole blood):

(1) CPDA-1 in the standard 1:8 ratio with whole blood.
(2) CPDA-1 in a 1:12 ratio with whole blood.
(3) CPDA-1 at 1:12 with 2 antithrombin units/mL hirudin in whole blood.
(4) CPDA-1 at 1:8 with 6 $\mu$M Thromstop in whole blood.
(5) No CPDA-1; 8 units/mL hirudin dissolved at 8× in 0.9% NaCl for a 1:8 ratio with whole blood, with dextrose and phosphate added at the levels in CPDA-1.
(6) No CPDA-1; 8 units/mL hirudin plus 300 nM PGE-1 and 1.9 mM theophylline with a $1 \times 10^{-4}$M 5-Amidinoindole dissolved at 8× in 0.9% NaCl for a 1:8 ratio with whole blood with dextrose and phosphate added at the levels in CPDA-1.
(7) No CPDA-1; 10 u/mL heparin plus 300 nM PGE-1 and 1.9 mM theophylline, dissolved at 8× in 0.9% NaCl for a 1:8 ratio with whole blood, with dextrose and phosphate added at the levels in CPDA-1.
(8) CPDA-1 at 1:8 with 300 $\mu$M PGE-1 and 1.9 mM theophylline in whole blood.
(9) Formula (8) with 20 anti-Xa units/mL Fragmin in whole blood.
(10) Formula (8) with 8 units/mL hirudin in whole blood.
(11) Formula (8) plus 348 kallikrein inhibitor units/mL aprotinin in whole blood.
(b 12) Formula (11) plus 6 $\mu$M Thromstop in whole blood.
(13) Formula (11) plus s units/mL hirudin in whole blood.
(14 Formula (11) plus $2 \times 10^{-5}$M DABE in whole blood.
(15) Formula (10) plus 40 $\mu$M BABIM.

Platelet Concentrate Preparation

Half-units (250 mL) of whole blood were collected from normal, healthy volunteer donors after informed consent was obtained according to the principles of the Declaration of Helsinki. This study was approved by the Institutional Review Committee for the protection of the rights of human subjects. A catheter fitted with a 17 gauge needle with a backeye (CD Medical, Miami Lakes, Fla.) was used for venepuncture. The first 30 mL of blood were discarded to avoid contamination of the blood bag with the tissue plug. Then a second catheter already inserted into the collection bag was quickly connected back-to-back with the first catheter to begin harvesting of blood. Platelet-rich plasma (PRP) was prepared by centrifugation of the whole blood at 22 degrees Centigrade in a Sorvall RC-3C with an H-6000 A rotor. The integrator was set for $8.2 \times 10^6$ rad$^2$/sec at a speed setting of 2210 rpm (1,420×gmax). The PRP was oentrifuged at 3000 rpm (2,620×gmax) at 22 degrees C. for 10 minutes to produce a platelet pellet. After a 60–90 minute "rest period," the pellet was resuspended in 30–40 mL of the supernatant platelet-poor plasma, based on the platelet count in PRP, to give a platelet concentration of approximately $1.3 \times 10^9$/mL in the PC. After resuspension, the PC was transferred sterilely to PL-732 containers with the surface area reduced to give either 7 or 4 cm$^2$/mL of PC as noted in the text. All PC were stored at 22 degrees C. on a flat bed, to-fro agitator. All samples were withdrawn with aseptic technique through sampling site couplers.

Test Tube PC

For each of 3 pilot experiments, sixteen 20 cc syringes were prefilled with 3 mL of various mixtures of citrate (CPDA-1), hirudin, and a phosphate-dextrose buffer. In rapid succession, each syringe was connected to a free-flowing 17 gauge catheter in the donor's vein and filled to the 20 cc mark. The whole blood was centrifuged at 700 ×g (max) for 8 minutes to make platelet-rich plasma, which was centrifuged at 2400 ×g (max) for 12 minutes to prepare a small PC. The pellet was resuspended, after a 60 minute waiting period, in 30% of the supernatant plasma and then sampled for platelet count, FPA level, and morphology score as described below.

Tests and Assays

The specific methodology employed for assessment of platelet function and integrity has been described in detail previously (Bode AP, Miller DT: *J Lab Clin Med* 1988; 111:118–124). FPA assays have also been described elsewhere (Bode AP, Miller DT: *Vox Sang* 1986; 51:192–196). In brief, platelet counts were determined on an electronic counter (Coulter Electronics S-Plus IV; Hialeah, Fla.) at several time points in the storage period to determine the percentage of single platelets remaining in each sample. Plasma pH, pO$_2$ (mmHg), and pCO$_2$ (mmHg) were determined at 37 degrees C. on a blood gas analyzer (Radiometer ABL Model 30: Copenhagen, Denmark).

The hypotonic shock recovery test was performed in a dual channel aggregometer (Payton Scientific; Buffalo, N.Y.) with a computer interface for on-line analysis. Aggregation response was measured on a Bio/Data PAP-4 four channel aggregometer (Hatboro, Pa.) with 1/10th volume ADP ($1 \times 10^{-5}$M, final). Each PC sample was diluted to approximately $3 \times 10^8$ platelets/mL in platelet-poor plasma prepared in trisodium citrate prior to aggregation testing. If PGE-1 and theophylline were present, the platelets were first centrifuged on an Eppendorf microfuge model 5415 for 1 minute at 14,000 rpm and then resuspended in inhibitor-free, trisodium oitrated plasma.

LDH (lactic dehydrogenase) assays were performed on PC supernatant plasma samples and on frozen-thawed whole PC samples by standard methodology on a Technicon RA-1000 for determination of percent LDH released during storage of PC. Glucose consumption in PC was calculated from measurements of the concentration of glucose in PC supernatant plasma using the glucose oxidase method on a Beckman Astra analyzer. The Day 10 or Day 15 value was subtracted from the Day 0 value to calculate the amount of glucose consumed per 10$^9$ platelets per day.

Platelet morphology was assessed by both light microscopy and transmission election microscopy. For routine monitoring of platelet morphology, PC samples were fixed with glutaraldehyde without prior washing steps to immobolize the platelets in a plasma gel for thorough visual examination and scoring (Bode AP, Miller DT: *J Lab Clin Med* 1988; 111:118–124). Each of two observers examined 200 platelets under 1000 x magnification on a microscope fitted with Nomarski differential interference contrast optics. The morphology score was reported as the percentage of platelets remaining in a smooth, discoid shape (averaged for both observers). For electron microscopy, PC samples were fixed in 9 vol half-strength Karnovsky's reagent (10) for 2 hours at room temperature, pelleted, then resuspended in 4% molten agar and centrifuged immediately to produce a tissue-like plug of platelets. The platelet pellet was post-fixed for 1 hour with 2% osmium tetroxide in 0.1M sodium cacodylate buffer, pH 7.4, at room temperature. The platelets were dehydrated through increasing ethanol and acetone and infiltrated with Epon-acetone and embedded by conventional procedures. Thin sections were cut with a diamond knife and stained with lead citrate and uranyl acetate prior to viewing in a Zeiss EM-109 Turbo transmission electron microscope at 50 kv.

Statistics

Comparison of grouped data (independent t-test, paired t-test or ANOVA) was carried out with a statistical software package (ABSTAT; Anderson-Bell, Canon City, Colo.) run on an IBM microcomputer.

RESULTS Hirudin

Hirudin is a naturally occurring, 65 amino-acid polypeptide excreted from the salivary glands of the leech *Hirudino medicinalis* with high affinity for thrombin (Markwardt F: *Ann N.Y. Acad Sci* 1986; 485:204–214). We placed the standard citrate anticoagulant with hirudin in an attempt to avoid the "irritating" effects of the low $Ca^{2+}$ environment in a citrated plasma (Kinlough-Rathbone RL, Packham Mass., Mustard JF; In: Harker LA, Zimmerman TS, eds. Methods of hematology: New York: *Churchill Livingstone* 1984:64-91). Several concentrations of hirudin were employed to anticoagulate half-units of whole blood, up to 8 antithrombin units/mL (Formula 5), without long-lasting success; the plasma remained fluid during preparation of PC, but clotted within 24 hours after blood collection. The platelet-poor plasma by-product of PC preparation did not clot spontaneously. The hirudin anticoagulant was further modified by addition of platelet-activation inhibitors and a Factor Xa inhibitor, 5-amidinoindole (Formula 6), but clotting of the PC still occurred within 16-50 hours of blood collection. Higher levels of hirudin were not used because of the high cost involved in anticoagulating large volumes of blood.

In a series of pilot experiments in test tubes, a matrix of 4 hirudin concentrations was crossed with 4 citrate:WB ratios to find an acceptable combination of reduced citrate levels with hirudin supplementation for further experimentation in PC. An analysis of variance (ANOVA) was performed on the results (Table 1) to determine the effect of reducing citrate or increasing hirudin in the anticoagulant. The statistically significant effects were limited solely to citrate concentration, none on hirudin concentration ($p > 0.2$). With decreasing citrate the FPA levels rose ($p = 0.0004$) and the (single) platelet count in the PC dropped ($p = 0.002$). The effect of decreasing citrate on platelet morphology was less significant, ($p = 0.03$).

TABLE 1

The effect of citrite:WB ratio and hirudin concentration on FPA levels, platelet count, and platelet morphology in a tube model of platelet concentrates.

| Hirudin[1] | Test | Citrate:WB Ratio | | | |
|---|---|---|---|---|---|
| | | 1:10 | 1:12 | 1:17 | 1:20 |
| 0 | Count[2] | 1.64 | 1.63 | 1.37 | 1.30 |
| | FPA[3] | 0 | 0 | 0 | 1.6 |
| | Morph[4] | 76% | 77% | 80% | 65% |
| 2 | Count | 1.25 | 1.42 | 1.46 | 1.18 |
| | FPA | 0.4 | 0 | 0 | 0.4 |
| | Morph | 65% | 72% | 74% | 67% |
| 6 | Count | 1.52 | 1.55 | 1.34 | 1.07 |
| | FPA | 0 | 0 | 0.3 | 2.1 |
| | Morph | 65% | 77% | 76% | 69% |
| 10 | Count | 1.57 | 1.60 | 1.33 | 1.15 |
| | FPA | 0 | 0.1 | 0.4 | 1.4 |
| | Morph | 74% | 79% | 74% | 74% |

[1] Hirudin concentration in whole blood (AT units per milliliter)
[2] Platelet count of resuspended PC, ($\times 10^9$ per milliliter)
[3] Fibrinopeptide A levels, in nanograms per milliliter
[4] Platelet morphology score, percent discs From these data, we concluded that the citrate:WB ratio could not be lowered below 1:12 without compromising the long-term in vitro viability of the PC, even with supplemental hirudin. We then prepared paired PC from each of two donors, one PC in the standard citrate:WB ratio of 1:8 (Formula 1) the other of each pair in a citrate:WB ratio of 1:12 (Formula 2) without or with hirudin (Formula 3). The results after a 7-day storage period, shown in Table 2, suggest that hirudin is needed to maintain the storage of platelets prepared with a reduced citrate:WB ratio. Extending the storage period to 10 days resulted in rapid deterioration in each PC, regardless of anticoagulant formula (data not shown).

TABLE 2

Function and integrity of platelets stored seven days in standard or reduced citrate, with or without supplementation with hirudin.

| Citrate:WB | Hirudin | pH | $pO_2$ | $pCO_2$ | morph[2] | Shock | Agg[3] ADP | FPA[5] AA | |
|---|---|---|---|---|---|---|---|---|---|
| 1:8 | 0 | 6.85 | 120 | 21 | 64% | 85% | 74% | 73% | 12 |
| 1:12 | 0 | 7.01 | 110 | 21 | 58% | 80% | rev[4] | rev[4] | 35 |
| 1:12 | 2 | 7.00 | 146 | 21 | 70% | 89% | 48% | 71% | 9 |

[1] Hirudin concentration in whole blood, AT u/milliliter
[2] Platelet morphology, percent discs
[3] Aggregation response (Vmax) as a percent of the response with fresh PC at Day 0
[4] Only reversible primary wave of aggregation observed
[5] Fibrinopeptide A levels in ng per milliliter Extended storage of PC was examined also in an anticoagulant formula (No. 4) containing citrate at the standard 1:8 ratio supplemented with a different thrombin inhibitor, Thromstop. Paired control and experimental PC were prepared in this experiment for each of two donors. The results after 10 days of storage (Table 3) indicate that the addition of Thromstop alone did not improve the quality of the PC, relative to matched controls.

TABLE 3

Lack of effect of 6 μM (final) Thromstop (Formula No. 4) on storage of PC for ten days at the standard 1:8 ratio of citrate:WB. Each experimental PC with CPDA-1 + Thromstop was paired with a control PC with CPDA-1 only (Formula No. 1).

|  |  | % Plts[1] | pH | $pO_2$ | $pCO_2$ | Shock[2] | LDH |
|---|---|---|---|---|---|---|---|
| Donor 1 | CPDA-1 + | 71% | 6.37 | 111 | 15 | 61% | 17% |
|  | Thromstop | 82% | 6.33 | 112 | 15 | 53% | 18% |
| Donor 2 | CPDA-1 + | 72% | 5.97 | 172[3] | 10[3] | 0 | 14% |
|  | Thromstop | 52% | 6.15 | 170[3] | 11[3] | 0 | 21% |

[1] Countable platelets remaining relative to the fresh PC at Day 0
[2] Hypotonic shock response expressed as a percent of the response in the fresh PC at Day 0
[3] These values of $pO_2$ $pCO_2$ represent approximate equilibration with room air

Heparin

In another approach to the elimination of citrate from the anticoagulant, unfractionated heparin was used in a phosphate-dextrose buffer to simulate the citrate formulation called CPD. (PGE-1 and theophylline were included (Formula 7) in an attempt to limit platelet clumping. The results (Table 4) were compared to those previously published (Bode AP, Miller DT: *J Lab Clin Med* 988; 111:118-124) for PC prepared and stored for 10-15 days in CPDA-1 plus PGE-1 and theophylline (Formula 8). This extended storage period was chosen for the comparison because of earlier success (Bode AP, Miller DT: *J Lab Clin Med* 1988; 111:118-124) in maintaining platelet in vitro viability for 15 days with Formula 8 plus thrombin inhibitors. Over this storage period, the platelet count of PC in heparin declined dramatically, suggesting that clumping of platelets continued even in the presence of PGE-1 and theophylline. With the exception of pH, the other markers also showed evidence of extensive loss of platelet function and integrity by Day 15 in all PC.

(Formula 9) over a 15 day storage period. The results (Table 4) again showed platelet clumping to be a major disadvantage to the use of heparin for preparation of PC. It would appear that the major decline in platelet function and integrity in the heparinized PC occurred after Day 10.

TABLE 4

Use of heparin in extended storage of PC.

|  | % plts[1] | pH | $pO_2$ | $pCO_2$ | Shock[2] | LDH | % Discs |
|---|---|---|---|---|---|---|---|
| Day 10 |  |  |  |  |  |  |  |
| Heparin (For. 7) | 63% | 7.31 | 174 | 14 | 98% | 35% | 24% |
| Citrate + Fragmin (For. 9) | 58% | 6.88 | 150 | 11 | 92% | ND | 23% |
| Citrate (For. 8) | 75% | 6.76 | 109 | 16 | 74% | 19% | 48% |
| Day 15 |  |  |  |  |  |  |  |
| Heparin (For. 7) | 33% | 6.82 | 186 | 8 | 38% | 43% | 16% |
| Citrate + Fragmin (For. 9) | 39% | 6.35 | 185 | 5 | 0 | ND | 4% |
| Citrate (For. 8) | 61% | 6.28 | 117 | 10 | 17% | 23% | 20% |

[1] Countable platelets remaining relative to the fresh PC at Day 0
[2] Hypotonic shock response expressed as a percent of the response in the fresh PC at Day 0

Aprotinin

Although the plasmin inhibitor aprotinin is not a high affinity inhibitor of thrombin or Factor Xa, its inhibition of Kallikrein in the contact activation system (Fritz H, Fink E, Truscheit E: *Federation Proc* 1979; 38:2753-2759) provides an anticoagulant capacity. The use of aprotinin in blood products previously was directed at its potential to reduce the incidence and severity of shock in transfusion (Lundsgaard-Hansen P: *Vox Sang* 1983; 45:1-5). There has been little or no data until now on its efficacy in long-term preservation of platelets. We added aprotinin to the experimental anticoagulant formula of CPDA-1 plus PGE-1 and theophylline (Formula 11) without and with other inhibitors (Formula Nos. 12-14) and compared the results to out previous "best" formulation without aprotinin (Formula 10). The data (Table 5) indicate that the formulations including aprotinin plus a thrombin inhibitor were superior.

TABLE 5

Storage of PC for 15 days in CPDA-1 containing PGE-1 and theophylline with or without aprotinin and/or a thrombin inhibitor; means only, n > 4 in each group.

| Additive(s)[1] | Formula | % Plts | pH | $pO_2$ | $pCO_2$ | Shock | ADP | LDH | % Discs |
|---|---|---|---|---|---|---|---|---|---|
| Hirudin | No. 10 | ND | 6.48 | 136 | 14 | 36% | 11% | 31% | 37% |
| Aprotinin | No. 11 | 69% | 6.41 | 116 | 22 | 65% | 0 | 20% | 52% |
| Aprotinin + 6 μM Thromstop | No. 12 | 70% | 6.55 | 103 | 25 | 66% | 76% | 11% | 68% |
| Aprotinin + 1 μM Thromstop | No. 12 (mod) | 77% | 6.27 | 126 | 20 | 59% | 26% | 8% | ND |
| Aprotinin + Hirudin | No. 13 | 67% | 6.46 | 85 | 29 | 87% | 42% | 11% | 70% |

[1] Additives to the basic anticoagulant formulation of CPDA-1 plus PGE-1 and theophylline (Formula No. 8)

Fractionation of heparin has reportedly led to preparations with reduced platelet interactions and yet adequate anticoagulant activity (Holmer E, Lindahl U, Baeckstroem G, Thunberg L, Sandgerg H, Soederstroem G, Andersson L-0: *Throm Res* 1980; 18: 861-869). We tested a low molecular weight heparin fragment, Fragmin (Kabi 2165), as an additive to citrate Statistical comparisons by t-test of Formula No. 10 versus pooled data from Formula Nos. 12 and 13 showed the latter to be superior in $pO_2$ (p=0.01), $pCO_2$ (p=0.001), hypotonic shock response (p=0.008), ADP-induced aggregation (p=0.003), percent LDH released (p=0.001), and percent discoid morphology (p=0.002). These PC were stored in PL-732 storage containers with a surface-to-volume ratio reduced to 4 cm$^2$/mL for reasons given elsewhere (Bode AP, Miller DT: *Vox Sang* 1988: (in review)). Platelet morphology after 15 days in PC prepared in Formula No. 12 is displayed in electron micrographs presented in FIG. 1. Small pseudopodia and slight irregularity of the cell surface were visible in many discoid platelets. A minority of platelets were highly vacuolated and degranulated.

A Factor Xa inhibitor, DABE, was also tested (n=4) in lieu of a thrombin inhibitor, with aprotinin (Formula 14). By Day 10 of storage, the platelets could no longer be aggregated with ADP nor recover from hypotonic shock, and the pH dropped to <6.0. Likewise, we added BABIM to the experimental anticoagulant with hirudin, but without aprotinin present (Formula 15). By Day 10 of the storage period, two of the four PC in this group were no longer responsive in the hypotonic shock test. By Day 15 all four PC were unresponsive and showed very poor morphology (<5% discs).

EXAMPLE 2

Use of Platelet Activation Inhibitors in Combination with Artificial Media for PC and Processes for Preparing Platelets in Artificial Media A series of extended platelet storage experiments using platelet activation inhibitors and a physiologic salt solution for the storage medium were conducted. The salt solution was developed by Dr. Stein Holme with Dr. Andrew Heaton at the American Red Cross Tidewater Region Blood Services (Norfolk, Va.), and it has been shown to provide improved platelet viability relative to platelet concentrate (PC) stored in plasma. The most successful design was to add platelet activation inhibitors directly to the platelet-rich plasma (PRP) before pelleting the platelets to make PC, then resuspending the platelets in the Norfolk medium supplemented with activation inhibitors.

In Table 6 below, results are presented for storage of PC prepared from PRP treated with 300 nM PGE-1 and 1.9 mM theophyline and stored in the NOrfolk medium containing 300 nM PGE-1 and 1.9 mM theophylline. These data indicate that platelet responsiveness and metabolic activity are preserved for as long as 20 days.

with inhibitors were conducted by adding compounds to the anticoagulant before blood collection. There are several advantages in adding the inhibitors to the PRP rather than to the anticoagulant: one, in the red blood cell transfusion products would not contain the inhibitors, and two lower concentrations of the inhibitors may suffice. We have prepared PC in the presence of the full cocktail of inhibitors (PGE-1+theophylline+Thromstop+aprotinin) added either to the anticoagulant or to the PRP. The results (Table 7) suggest that better platelet responsiveness is maintained during storage when the inhibitors are added to the PRP rather than to the anticoagulant.

TABLE 7

Storage of PC (n = 4) in the presence of 300 nM PGE-1 + 1.9 mM theophylline + 6 µM Thromstop + 348 KIU per milliliter aprotinin added to either the anticoagulant ("WB-Inhib") to produce the given concentrations in whole blood or added to the PRP ("PRP-Inhib") to give the same final concentrations. The PC were subsequently stored 15 days in the Norfolk medium supplemented with the inhibitors at the concentrations given above. Surface-to-volume ratio = 4 cm$^2$ per milliliter.

|  | % Plts[1] | pH | pO$_2$ | pCO$_2$ | Shock |
|---|---|---|---|---|---|
| WB-Inhib | 65% | 7.23 | 127 | 33 | 39% |
| PRP-Inhib | 90% | 6.96 | 60 | 39 | 94% |

[1]Percent platelets remaining relative to Day 0.

In studies extending the results reported above, units of non-aspirinated CPDA-1 whole blood were selected at random from Red Cross bloodmobiles and centrifuged to make platelet-rich plasma in our laboratory. To the PRP was added one eighth volume of citrated saline containing the supplement of inhibitors, such as PGE-1 and theophylline, dissolved at high concentrations in the citrated saline to give effective levels in the PRP equivalent to those obtained in blood from modified CPDA-1. After a short incubation (15-30 minutes) the PRP was centrifuged to make a platelet pellet which was resuspended in the Norfolk artificial medium containing another dose of the inhibitors. This approach seemed to be more effective than the use of inhibitors in whole blood, possible due to metabolizing of PGE-1 by RBCs and thus a decrease in the effect of this inhibitor on platelets.

Data obtained through the addition of PGE-1 plus theophylline to PRP and the Norfolk medium are pres-

TABLE 6

In vitro viability of PC (n = 10) prepared from PRP treated with 300 nM PGE-1 and 1.9 mM theophylline and stored in the Norfolk medium supplemented with 300 nM PGE-1 and 1.9 mM theophylline. Surface-to-volume ratio = 4 cm$^2$ per milliliter.

|  | pH | pO$_2$ | pCo$_2$ | Shock[1] | LDH[2] | Lactate | Glucose |
|---|---|---|---|---|---|---|---|
| Day 15 | 7.04 | 82 | 33 | 79% | 12% | 31 mM | 188 mg/dL |
| Day 20 | 6.72 | 102 | 21 | 58% | 17% | 39 | 101 |
| Standard PC Day 15 | <6.0 | 180 | 7 | 0% | 67% | 43 | 19 |

[1]Hypotonic shock recovery test; result expressed as a percent of the Day 0 response
[2]Released lactic dehydrogenase; result expressed as a percent of total LDH measured in frozen-thawed platelet suspensions Apparently, the addition of PGE-1 and theophyline to the PRP is sufficient to inhibit platelet activation during the PC preparation phase. Our previous studies ented in Table 8. A further improvement was noted with the addition of aprotinin and Thromstop to the PGE-1 plus theophylline cocktail (see Table 9).

TABLE 8

PC stored in PAS + glucose (the Norfolk medium) with 300 nM PGE-1 plus 1.9 mM theophylline (n = 10).

| | Count[1] | pH | pO$_2$ | pCO$_2$ | Shock[2] | Glucose | Lactate | % LDH[3] |
|---|---|---|---|---|---|---|---|---|
| Day 1 | 1.20 | 7.18 | 34 | 89 | 0.090 | 532 mg/dL | 2.6 mM | 2% |
| Day 15 | 80% | 7.04 | 82 | 33 | 79% | 188 mg/dL | 31 mM | 12% |
| Day 20 | 69% | 6.72 | 120 | 21 | 58% | 101 mg/dL | 40 mM | 17% |

[1]Platelet count expressed per 10$^9$/mL; Day 15 and Day 20 value expressed as a percent of Day 1
[2]Hypotonic shock recovery rate expressed as delta-OD/min; Day 15 and Day 20 value expressed as a percent of Day 1
[3]Released LDH expressed as a percent of total cellular LDH

TABLE 9

PC stored in PAS + glucose (the Norfolk medium) with 300 nM PGE-1 + 1.9 mM theophylline + 348 KI u/mL aprotinin + 6 μM Thromstop (n = 6).

| | Count[1] | pH | pO$_2$ | pCO$_2$ | Shock[2] | Glucose | Lactate | % LDH[3] |
|---|---|---|---|---|---|---|---|---|
| Day 1 | 1.20 | 7.09 | 15 | 99 | 0.091 | 522 mg/dL | 3 mM | 2% |
| Day 15 | 97% | 6.78 | 75 | 37 | 78% | 179 mg/dL | 28 mM | 6% |
| Day 20 | 90% | 6.56 | 130 | 24 | 62% | 92 mg/dL | 36 mM | 10% |

[1]Platelet count expressed per 10$^9$/mL; Day 15 and Day 20 value expressed as a percent of Day 1
[2]Hypotonic shock recovery rate expressed as delta-OD/min; Day 15 and Day 20 value expressed as a percent of Day 1
[3]Released LDH expressed as a percent of total cellular LDH

EXAMPLE 3

REDUCED PHOSPHATE IN ARTIFICIAL MEDIA CONTAINING PLATELET ACTIVATION INHIBITORS

We also tested a modification of the Norfolk medium to reduce the amount of phosphate ion; the CPD reagent in the medium was replaced with ACD (pO$_4$-free) and 10% more sodium bicarbonate was added to equilibrate the pH. The phosphate ion concentration was reduced to examine its effect on platelet metabolism during storage. The results (Table 10) suggest that the reduction in phosphate was beneficial in lowering the metabolic rate of stored platelets without compromising function and integrity.

TABLE 10

PC stored in PAS + glucose + 300 nM PGE-1 and 1.9 mM theophylline with ACD substituted for CPD in PAS (n = 3).

| | Count[1] | pH | pO$_2$ | pCO$_2$ | Shock | Glucose | Lactate | % LDH[3] |
|---|---|---|---|---|---|---|---|---|
| Day 1 | 1.40 | 6.94 | 32 | 127 | 0.122 | 556 mg/dL | 4.6 mM | 1% |
| Day 15 | 96% | 6.72 | 53 | 37 | 82% | 192 mg/dL | 31 mM | 6% |
| Day 20 | 93% | 6.66 | 97 | 29 | 73% | 123 mg/dL | 33 mM | 8% |

[1]Platelet count expressed per 10$^9$/mL; Day 15 and Day 20 value expressed as a percent of Day 1
[2]Hypotonic shock recovery rate expressed as delta-OD/min; Day 15 and Day 20 value expressed as a percent of Day 1
[3]Released LDH expressed as a percent of total cellular LDH Other formulations of inhibitors were tried in the use of the Norfolk artificial medium for extended storage of platelets; none proved as effective as those described in Tables 8–10. These attempts included preparations with 100 μM caffeine with and without PGE-1, 300 nM PGE-1 without theophylline, 300 nM PGE-1 with 1 mM theophylline (half-strength), 10 μM trifenagrel (an inhibitor of the cyclo-oxygenase enzyme system in platelets), forskolin at several concentrations, and changes in methodology such as, adding PGE-1 plus theophyline to the PRP only or to the PC only instead of at both steps. The lack of success with these maneuvers illustrates the extent of the role of platelet activation in the storage lesion.

EXAMPLE 4

Influence of Surface-to-Volume Ratios

In our first studies on the addition of platelet activation inhibitors to the citrate anticoagulant for plasma PC, we used the standard ratio of bag surface to PC volume of 7 cm$^2$ per milliliter. Upon noting a decrease in lactate build-up and glucose consumption in PC as a result of the inhibitors, we decided to see how much we could minimize the bag surface area before compromising gas exchange across the bag wall. To accomplish this strategy experimentally, we rolled up the PL-732 storage container length-wise and secured it with metal clips before introducing PC into the bag for storage. The initial experiments were done with the formulation of CPDA-1 modified with 300 nM PGE-1 plus 1.9 mM theophylline and 348 KI units per milliliter aprotinin (final concs. in PRP); the PC were stored in their native plasma (containing the inhibitors) at surface-to-volume (S/V) ratios of 7, 4 and 2 cm$^2$ per milliliter. The results (Table 14) showed a remarkable effect of S/V ratio on the outcome after 15 days of storage of these PC. The best S/V ratio appeared to be 4 cm$^2$ per milliliter, which was later confirmed for other formulations of inhibitors.

TABLE 11

Effects of surface-to-volume ratio in PC stored in CPDA-1 + PGE-1 + theophylline + aprotinin for 15 days (Means, N = 4 each group).

| S/V | Percent Plts Remaining | pH | pCO$_2$ | pO$_2$ | % Hypo Shock Remaining |
|---|---|---|---|---|---|
| 2 | ND | 5.87 | 7 | 187 | 0% |

TABLE 11-continued

Effects of surface-to-volume ratio in PC stored in CPDA-1 + PGE-1 + theophylline + aprotinin for 15 days (Means, N = 4 each group).

| S/V | Percent Plts Remaining | pH | pCO$_2$ | pO$_2$ | % Hypo Shock Remaining |
|---|---|---|---|---|---|
| 4 | 61% | 6.58 | 18 | 135 | 81% |
| 7 | 31% | 6.61* | 9 | 180 | 19% |

*PC having pCO$_2$ ≤ 10 and pO$_2$ ≥ 180 mm Hg and minimal or no response to hypotonic shock are probably not of value for transfusion even if the pH is still above 6.0.

The beneficial effect of a reduced S/V ratio was used to advantage in all of the successful formulations of inhibitors for PC stored in plasma and for PC stored in artificial media. The data reported in Tables 8–11 of this report were generated with PC stored at S/V =4. When control studies were performed at reduced S/V ratios without platelet activation inhibitors, the results indicated no beneficial effect due solely to a reduction in surface area (data not shown). It would appear also, mostly from the data in Table 11 and other similar experiments, that the full beneficial effect of the platelet activation inhibitors cannot be realized until the S/V ratio is lowered to take advantage of the lower metabolic rate and reduced need for gas exchange across the storage container. Possibly, this effect is mediated by a reduction in the rate of exposure of stored platelets to a foreign surface, namely the bag wall, by reducing the available surface area with which the platelets can interact. The ability of the inhibitors to prevent activation by this route may be greatly enhanced when the number of collisions of platelets with the bag wall is statistically reduced by this method.

The foregoing examples are illustrative of the present invention, and are not to be taken as restrictive thereof. The invention is defined by the following claims, with equivalents of the claims to be included therein.

That which is claimed is:

1. A blood platelet preparation, comprising:
   blood platelets;
   an adenylate cyclase stimulator in an amount effective to increase the production of adenosine 3', 5'cyclic phosphate (cAMP) in said blood platelets;
   a phosphodiesterase inhibitor in an amount effective to reduce the degradation of cAMP in said blood platelets;
   a thrombin inhibitor in an amount effective to reduce the stimulation of said blood platelets by thrombin; and
   a plasmin inhibitor in an amount effective to reduce the degradation of cell surface proteins on said blood platelets.

2. A blood platelet preparation as claimed in claim 1, wherein said preparation further comprises blood plasma.

3. A blood platelet preparation as claimed in claim 1, wherein said preparation comprises a platelet concentrate.

4. A blood platelet preparation as claimed in claim 1, wherein said preparation is a plasma-free preparation.

5. A blood platelet preparation according to claim 1, wherein said adenylate cyclase stimulator is prostaglandin E1.

6. A blood platelet preparation according to claim 1, wherein said phosphodiesterase inhibitor is theophylline.

7. A blood platelet preparation according to claim 1, wherein said thrombin inhibitor is selected from the group consisting of hirudin and N-(2-naphthylsulfonylglycyl)-D,L-amidinophenylalaninpiperidine.

8. A blood platelet preparation according to claim 1, wherein said plasmin inhibitor is aprotinin.

9. A blood platelet preparation according to claim 1, wherein said adenylate cyclase stimulator is prostaglandin E1:
   wherein said phosphodiesterase inhibitor is theophylline;
   wherein said thrombin inhibitor is selected from the group consisting of hirudin and N-(2-naphthylsulfonylglycly)-D,L-amidinophenylalaninpiperidine;
   and wherein said plasmin inhibitor is aprotinin.

10. A blood platelet preparation according to claim 1 or 9 in a container having a surface to volume ration of between about 3 to 5 square centimeters per milliliter.

11. A blood platelet preparation according to claim 1 or 9 in a container having a surface to volume ration of about 4 square centimeters per milliliter.

* * * * *

UNITED STATES PATENT AND TRADEMARK OFFICE
CERTIFICATE OF CORRECTION

PATENT NO. : 4,994,367
DATED : 19 February 1991
INVENTOR(S) : Arthur Palfrey Bode et al.

It is certified that error appears in the above-identified patent and that said Letters Patent is hereby corrected as shown below:

TITLE PAGE:
In the "Inventors" section, William Andrew Lambert Heaton and Stein Holme should be deleted.

Column 1, line 34, "Sano." should read --Sang.--.

Column 5, line 48, "plus s" should read --plus 8--.

Column 5, line 50, "(14" should read --(14)--.

Column 6, line 4, "oentrifuged" should be spelled --centrifuged--.

Column 6, line 57, "oitrated" should be spelled --citrated--.

Column 9, line 34, "Med 988" should read --Med 1988--.

Column 11, line 42, "NOrfolk" should read --Norfolk--.

Column 12, line 8, "+-'" should read --+--.

Column 13, line 32, "(pO$_4$-free)" should read --(PO$_4$-free)--.

Column 13, line 43, Table 10, the fifth column heading "Shock" should read --Shock$^2$--.

Column 15, line 9, Table 11, "$\leq$" and "$\geq$" should read --$\leq$-- and --$\geq$--.

Signed and Sealed this

Eighth Day of September, 1992

Attest:

DOUGLAS B. COMER

Attesting Officer

Acting Commissioner of Patents and Trademarks

UNITED STATES PATENT AND TRADEMARK OFFICE
CERTIFICATE OF CORRECTION

PATENT NO. : 4,994,367
DATED : February 19, 1991
INVENTOR(S) : Bode et al.

It is certified that error appears in the above-identified patent and that said Letters Patent is hereby corrected as shown below:

Column 1, line 5, before BACKGROUND OF THE INVENTION, please insert,

-- This invention was made with Government support under Contract DAMD17-86-C-6180 awarded by the U.S. Army Medical Research Acquisition Activity (USAMRAA). The government has certain rights in this invention.--

Signed and Sealed this

Twenty-fifth Day of May, 1999

Attest:

Q. TODD DICKINSON

*Attesting Officer*  *Acting Commissioner of Patents and Trademarks*